United States Patent
Härer et al.

(10) Patent No.: US 7,796,723 B2
(45) Date of Patent: Sep. 14, 2010

(54) METHOD FOR PROVIDING 3D IMAGE DATA AND SYSTEM FOR TAKING X-RAY IMAGES

(75) Inventors: Wolfgang Härer, Erlangen (DE); Michael Zellerhoff, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 123 days.

(21) Appl. No.: 11/888,882

(22) Filed: Aug. 2, 2007

(65) Prior Publication Data

US 2008/0031403 A1  Feb. 7, 2008

(30) Foreign Application Priority Data

Aug. 3, 2006 (DE) .................. 10 2006 036 327

(51) Int. Cl.
*A61B 6/03* (2006.01)
(52) U.S. Cl. .......................... 378/26; 378/11
(58) Field of Classification Search .............. 378/4, 378/197, 11, 21, 22, 26
See application file for complete search history.

(56) References Cited

U.S. PATENT DOCUMENTS

| | | | | |
|---|---|---|---|---|
| 3,924,131 A * | 12/1975 | Hounsfield | .................... | 378/11 |
| 4,639,941 A * | 1/1987 | Hounsfield | .................... | 378/11 |
| 4,920,491 A * | 4/1990 | Eberhard et al. | ............ | 378/901 |
| 5,276,614 A * | 1/1994 | Heuscher | .................... | 382/260 |
| 5,386,453 A * | 1/1995 | Harrawood et al. | ......... | 378/196 |
| 5,611,026 A | 3/1997 | Eberhard et al. | | |
| 6,442,288 B1 | 8/2002 | Haerer et al. | | |
| 2002/0037068 A1 * | 3/2002 | Oikawa | ........................ | 378/15 |
| 2002/0090051 A1 | 7/2002 | Oikawa | | |
| 2002/0154727 A1 * | 10/2002 | Ning | .............................. | 378/4 |
| 2003/0099330 A1 * | 5/2003 | Mery et al. | ................. | 378/210 |
| 2005/0058240 A1 * | 3/2005 | Claus | ........................... | 378/22 |
| 2006/0056577 A1 | 3/2006 | Hunt et al. | | |
| 2007/0268994 A1 * | 11/2007 | Chen | ............................. | 378/4 |

FOREIGN PATENT DOCUMENTS

| | | |
|---|---|---|
| DE | 19842944 A1 | 7/1999 |
| DE | 10 2005 050 917 A1 | 4/2007 |
| EP | 1 635 168 A2 | 3/2006 |

OTHER PUBLICATIONS

G.L. Zeng, "Image Reconstruction—a Tutorial", Computerized Medical Imaging and Graphics 25, 2001, pp. 97-103, Pergamon, Elsevier Science Ltd.
Günter Lauritsch and Wolfgang H. Härer, "A Theoretical Framework for Filtered Backprojection in Tomosynthesis", Proceedings of the SPIE Medical Imaging Conference, Improcessing 3338, San Diego, CA, Feb. 21-27, 1998, pp. 1127-1137.

(Continued)

*Primary Examiner*—Chih-Cheng G Kao

(57) ABSTRACT

In a known type of tomosynthesis x-ray source and x-ray detector are linearly moved and x-rays images are taken for a large number of positions, the images being reconstructed to give a 3D image record. According to the invention x-ray source and x-ray detector are swiveled and a sequence of x-rays is subsequently taken again, x-ray source and x-ray detector again being moved in a straight line. One drawback of simple tomosynthesis with movement in a straight line is suppressed thereby, the drawback being that the quality of reconstruction is particularly poor in a certain direction.

20 Claims, 1 Drawing Sheet

OTHER PUBLICATIONS

Zellerhoff et al., Low contrast 3D-reconstruction from C-arm data, Medical Imaging, Physics of Medical Imaging, Proceedings of SPIE, 2005, pp. 646-655, vol. 5745.

Härer et al.: Tomographie—Prinzip und Potential der Schichtbildverfahren In Th. Schmidt (Hrsg.), Diagnostic Radiology Handbook, 2003, pp. 1-18, vol. 1, Chapter 2.4 Springer Verlag, Berlin, Heidelberg, ISBN: 3-540-41419-32.4.

* cited by examiner

METHOD FOR PROVIDING 3D IMAGE DATA AND SYSTEM FOR TAKING X-RAY IMAGES

CROSS REFERENCE TO RELATED APPLICATIONS

This application claims priority of German application No. 10 2006 036 327.2 filed Aug. 3, 2006, which is incorporated by reference herein in its entirety.

FIELD OF THE INVENTION

The invention relates to a method for providing 3D image data of an object, in particular a patient and to a system for taking x-ray images.

BACKGROUND OF THE INVENTION

A method of this type is known by the name of tomosynthesis. A sequence of x-ray images is taken. In order not to keep taking the same x-ray images the relative position between x-ray source and object is varied in each case. In this case this takes place in such a way that the x-ray source is moved in a straight line. Since in an x-ray source method the x-ray detector is conventionally not large enough to always receive the x-rays which have penetrated the patient's body, the x-ray detector is conventionally also moved in a straight line. The movement in a straight line of x-ray source and x-ray detector is coordinated, i.e. coupled. The x-ray detector can be moved in the same direction as the x-ray source or in the opposite direction thereto. As an alternative to moving at least the x-ray source and optionally also the x-ray detector, the object may also be moved in a straight line. As a rule this is done in such a way that the patient table, on which the patient is situated, is moved. Of course it is also possible for x-ray source/x-ray detector and the object to be moved in a straight line simultaneously.

Computer tomography (CT) is a method that differs from tomosynthesis and one in which a large number of x-ray images is taken. Characteristic of CT is that the image density and the area from which the images are obtained are sufficiently high or great to allow an exact reconstruction of the imaged object by 3D image data within the framework of image resolution. A CT image record can thus be designated complete. Characteristic of tomosynthesis is that the image data is not complete, i.e. that there are basically limitations to the quality of the reconstruction. This is opposed by the advantage of tomosynthesis that considerably fewer x-ray images from a much smaller area are taken overall, whereby tomosynthesis can be carried out much quicker than CT and owing to the smaller area has advantages in terms of patient accessibility.

Said type of tomosynthesis, in which the imaging system or the patient is moved in a straight line, demonstrates drawbacks in resolution quality, in particular in an especially marked direction. This direction is defined by a connecting line between the respective axes of movement in the case of moveable x-ray source and movable x-ray detector. When using a flat-panel x-ray detector this connecting line defines the same direction as the surface normal of the flat-panel x-ray detector.

SUMMARY OF THE INVENTION

The object of the invention is to eliminate the drawback of poor resolution in the marked direction without losing the advantages of tomosynthesis.

This object is achieved by a method and a system as claimed in the claims.

According to the invention, after taking the first sequence of x-ray images (with the straight-line method), at least once a) the x-ray source and the x-ray detector are swiveled and b) a farther sequence of x-ray images is taken for which the x-ray source, possibly coupled to the x-ray detector, and/or the object is/are moved in a straight line.

With the aid of the x-ray images of the first and all subsequent sequence(s) the 3D image data is then generated using a (predefined) reconstruction method.

At least two tomosynthesis x-ray image sequences are thus taken. By swiveling the x-ray image source and x-ray detector the two sequences differ in that the direction in which the quality of resolution is particularly poor changes. If all image data is now used for reconstruction, a certain equalization takes place, and the overall result is improved resolution. While the number of x-ray images is at least doubled, if not trebled or quadrupled even, compared with the number of x-ray images which are taken with a conventional CT the total number of x-ray images can still be much lower, so the advantage of tomosynthesis is retained in that the 3D image data is available much more quickly. The claimed form of movement (straight-line movement—swiveling—straight-line movement, etc.) is also more efficient than the scanning conventionally used in CT in which the system is rotated about the longitudinal axis of the patient's body and a large number of x-ray images is taken in each case, a displacement (of system or patient) subsequently taking place, then repeated rotation of the system, etc.

In principle it is possible for the straight-line movement to not always run in the same direction in the various sequences of x-ray images, although it is preferred if a single axis is established, along which the straight-line movement takes place for all x-ray image sequences. A natural consequence of this is that x-ray source and x-ray detector are swiveled exactly about this axis.

In the present case an axis for the straight-line movement is mentioned, along which axis the movement takes place. This should be understood in such a way that the axis predefines the direction of movement but not the exact location of the respectively moved devices. Naturally a large number of parallel axes of this kind may be defined and it is clear that x-ray source and x-ray detector are swiveled about only one axis from this large number of axes. Said embodiment has the advantage that the motors for straight-line movement and optionally for swiveling can be designed particularly simply.

In a preferred embodiment, with every further sequence of x-ray images the x-ray source is in each case moved with the x-ray detector or object in a direction opposite to the direction adopted during the previous sequence of x-ray images. In short this means that they are moved back and forth once. Reversing the direction of movement from sequence to sequence prevents the apparatus from always having to be returned to a starting point again. Of course time is gained thereby when taking the images.

Previous conventional x-ray equipment does not allow the claimed form of movement. In a preferred embodiment of the invention a robot arm is used to which the x-ray source and x-ray detector are fastened and on which they can swivel about a swiveling axis, it being possible for the robot arm to move along the swiveling axis.

In combination with a conventional x-ray C-arm system it may be provided that when taking sequences of x-ray images a patient table, on which the patient is situated, is moved along a swiveling axis of the x-ray C-arm. The x-ray C-arm can be conventionally swiveled about its swiveling axis between taking of sequences.

It is not necessarily the case that X=ray source and x-ray detector have to be moved in the same direction, instead it is also possible for them to be moved in opposite directions. For this purpose x-ray source and x-ray detector for example can each be secured to different x-ray robot arms which can each allow swiveling and can move linearly.

Basically any reconstruction method conventional in tomosynthesis and known per se from the prior art can be used as the reconstruction method in the invention. For example a 3D image record with entries for a large number of partial volumes can be generated from each sequence of X=ray images. The entries are subsequently added to all sequences of x-ray images for each partial volume. There is then no distinction between x-ray images of one sequence and another.

An example of a reconstruction method which is basically known is the method of filtered back projection. This is described for example in the review article by G. L. Zeng "Image reconstruction—a tutorial", Computerized Medical Imaging and Graphics 25 (2001), pages 97 to 103. Further information on filtered back projection can also be found in the article by G. Lauritsch and W. Härer, "A theoretical framework for filtered backprojection in tomosynthesis" in: Hanson K M (ed.), Medical Imaging 1998: Image Processing vol. 3338, SPIE, Bellingham (USA), pages 1127 to 1137. With back projection a model volume of the object for imaging is assumed and the x-ray which generated the image information at a certain data point in the x-ray image is retraced. This image information is nothing more than a numerical value which represents the absorption through the imaged object along the ray being considered. Within the framework of back projection it is assumed that absorption takes place uniformly through the body, and for reconstruction of this body partial volumes of the body model are each associated with part of the numerical value which is defined by equal distribution. If back projection is carried out for a large number of images partial volumes of the model body result, in which the values add up to high values, as well as areas in which there are hardly any overlaps. If back projection is thus carried out for a large number of x-rays information about the structure of the imaged body is obtained. As mentioned above, tomosynthesis does not allow exact reconstruction, i.e. reconstruction which is just as accurate as the resolution of the imaging system. An improvement is obtained by filtering. In this connection either each x-ray image is filtered individually using a filter or the 3D image record is subjected to filtering. Compound filters may also be used, i.e. filters which act successively on the frequency spectrum, in other words multiplied—see for example the above-mentioned article by Lauritsch and Härer. It is not important whether some of these filters are applied to the x-ray images and some of these images to the 3D image data, or whether all of the filters are applied to only the x-rays images or only the 3D image data respectively.

The filter must of course contain a form of information about the imaging conditions. In the case of the present invention therefore the definition of such filters may be particularly well established if a separate filter is used for each sequence of x-ray images. Since each sequence of x-ray images represents an individual tomosynthesis in the prior art, definition of a filter of this kind is particularly easy.

In a modified, advantageous version only a single overall filter is used for a sequences of x-ray images. This filter therefore also contains the information about all swivel movements of x-ray source and x-ray detector.

In the prior art filters are often analytically determined for filtered back projection. A geometric model of the imaging system is used in this connection and there are methods known per se of defining a filter with this aid of this model—see also the above-mentioned article by Lauritsch and Härer in this regard. Since the analytical method becomes more complicated by including swiveling, a method for defining filters for filtered back projection which is described in DE 10 2005 050 917, published after the application date of the present application, can become more important. In this connection the filter is provided in that test objects that are known in terms of their 3D structure are used and x-ray image data is generated for each test object. Since the 3D structure of the test objects is known, 3D image data can be generated from the x-ray images and compared with the known 3D structure. Applied to 3D image data (or previously to the x-ray images) the filter should then cause the resulting 3D image data to exactly match the known 3D structure of the test object after filtering.

The complete method, as it is described above according to the invention, is therefore carried out on the test objects, only using the test object instead of the object. Execution can take place in real terms or virtually as a computer simulation. By comparing the 3D image data obtained in this connection with the known 3D structure of the test object a filter is subsequently determined which is thereafter used in the x-ray images of the object to generate (reconstruct) the 3D image data. When executing the method using the test objects the procedure should be the same as subsequently with the object or patient. In other words, the movement positions should be defined in advance and then used for the test object and subsequently for the object/patient as well.

Instead of the filtered back projection a method may also be used which is known per se in the prior art as an iterative method and has been used in particular in the early days of CT. This method is also described for example in the above-mentioned article by Zeng. With iterative methods a sequence of what are known as "forward projections", i.e. the calculation of projections from an image volume and back projections, is used as in CT. To start with an approximate image is provided which, for example, can consist of a constant pre-allocation. Projections are then calculated from this image and the differences thereof from the measured projections determined. The differential images are back-projected and, more precisely, for all x-ray images. An improved approximate image record is thus obtained for the 3D image data to be attained. New forward projections can be generated from this approximation, then the difference established again, etc. The data does not change any further after a finite number of iterations (the differences reach zero) and the 3D image record then attained is the final result of the iterative method. As is known the iterative method has the advantage of high precision and the drawback of high calculational effort compared with filtered back projections.

The invention is also embodied by a system for taking x-ray images, comprising a robot arm to which an x-ray source and an x-ray detector are fastened. The robot arm can move along an axis and can be pivoted about the axis. Said system for the first time allows a coordinated lengthwise movement of x-ray source and x-ray detector for a large number of swivel positions.

To carry out the method according to the invention the system should comprise a control unit which is designed to activate x-ray source and x-ray detector and to drive a motor for moving and swiveling the robot arm. The control unit should moreover be programmed in such a way that the method according to the invention can be carried out in an automatic sequence.

Use of a reconstruction method which accompanies the calculation steps also forms part of the method according to the invention. To execute these calculational steps the control unit should comprise a calculational unit for evaluating the x-ray images and be correspondingly programmed, in particular programmed in such a way to use the above-mentioned reconstruction methods.

BRIEF DESCRIPTION OF THE DRAWINGS

A preferred embodiment of the invention will be described hereinafter with reference to the drawings, in which.

DETAILED DESCRIPTION OF THE INVENTION

Figure 1:
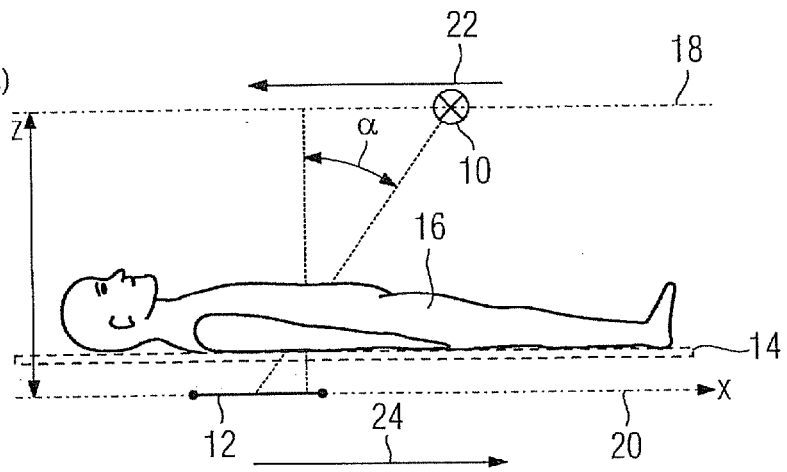
FIG. 1 shows the arrangement of the imaging units in a first tomosynthesis method according to the prior art.

The FIGS. each show an x-ray system, an x-ray tube 10, serving as x-ray source, and a flat-panel x-ray detector 12 each being shown by symbols. A broken line symbolically illustrates a patient table 14 on which a patient 16 is situated.

In tomosynthesis a sequence of x-ray images if taken using the x-ray tube 10 and the flat-panel x-ray detector 12. The position of x-ray tube 10 and flat-panel x-ray detector 12 changes from image to image. With the type of tomosynthesis shown in FIG. 1 and FIG. 2, which is the basis for the present invention, the x-ray tube 10 is moved on a linear path, namely along an axis 18. The flat-panel x-ray detector 12 is also linearly moved, namely along an axis 20. The axes 18 and 20 are parallel.

Figure 2:
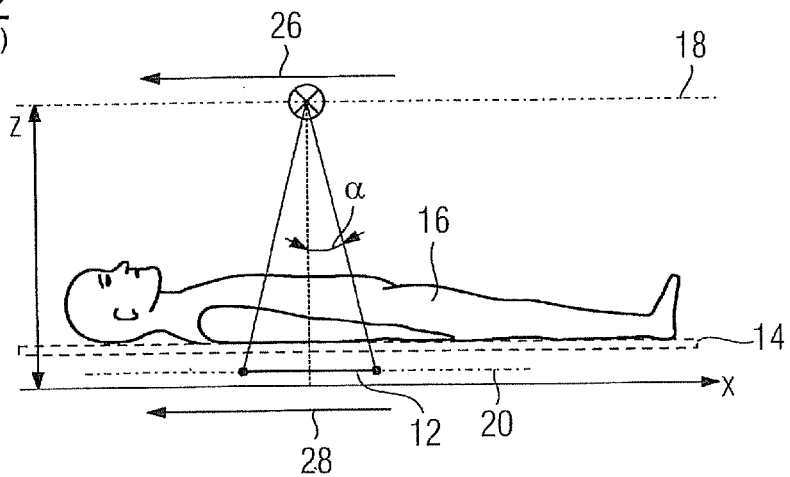
FIG. 2 shows the arrangement of the imaging units in a second tomosynthesis method according to the prior art, and FIG. 3 schematically shows the position of the imaging units according to the invention.

FIG. 1 and FIG. 2 relate to different types of relative movement of x-ray tube 10 and flat-panel x-ray detector 12. FIG. 1 shows an arrow 22 which indicates the direction of movement of the x-ray tube 10. An arrow 24 shows the direction of movement of the flat-panel x-ray detector 12. X-ray tube 10 and flat-panel x-ray detector 12 are thus moved in opposite directions. FIG. 2 shows an arrow 26 which indicates the movement of the x-ray tube 10, and an arrow 28 which indicates the movement of the flat-panel x-ray detector 12. In the case of FIG. 2 x-ray tube 10 and flat-panel x-ray detector 12 are moved in the same direction. The present invention can make use of both types of movement.

Both FIGS. 1 and 2 show the tomosynthesis angle α respectively. This is defined between a straight line, which connects the x-ray tube 10 with a center point of the flat-panel x-ray detector 12, and a straight line, which connects the two straight lines 18 and 20 to each other and is perpendicular thereto. The z axis is shown, with respect to which the angle α is defined. This axis is also the surface normal of the flat-panel x-ray detector 12. The tomosynthesis is characterized in that α never reaches 90°, i.e. that the x-ray tube 10 is moved to a finite extent on the straight line 18. For complete imaging of the patient 16 which allows exact reconstruction of the structure of the patient 16 within the framework of imaging accuracy, the tomosynthesis angle α must not be limited. However, in order to save time only a limited number of x-ray images is taken from a limited angle range with tomosynthesis.

Common to both types of tomosynthesis described with reference to FIGS. 1 and 2 is that the quality of the reconstruction of a 3D image record, which is intended to represent the patient 16, is poor inter alia, and this is a resolution along the z axis.

Figure 3:
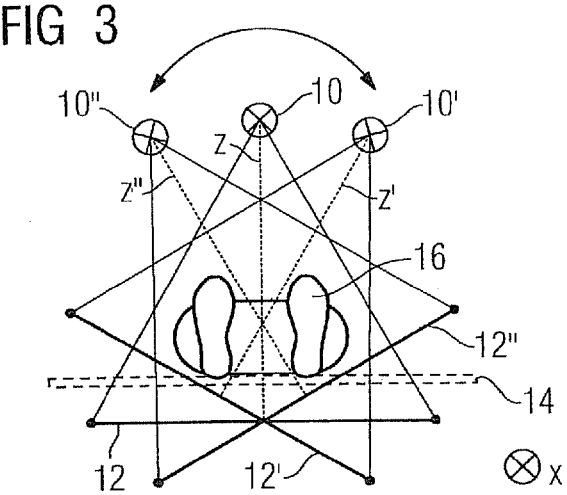

The invention solves this problem in that x-ray tube 10 and flat-panel x-ray detector (together) are swiveled about an axis (not specially identified) parallel to the straight lines 18 and 20, i.e. in a plane perpendicular to the direction of movement. On swiveling the x-ray tube 10 in FIG. 3 to the right, the x-ray tube 10 adopts a different position and so it can be better discerned this is designated 10'. On swiveling to the left it adopts a position where the x-ray tube is designated 10". The flat-panel x-ray detector is analogously tilted so it adopts the positions 12' and 12".

A first x-ray image sequence is taken in the basic state in the invention. Swiveling then takes place. A further x-ray image sequence is then taken, for example in the state designated by single lines. Further x-ray image sequences can then be taken, for example after repeated swiveling into the state which is identified by double lines. Partial tomosyntheses are thus effectively carried out according to FIG. 1 or FIG. 2 in each case. The partial tomosyntheses differ in that the direction in which the imaging quality is particularly poor changes. This direction was the z axis in FIGS. 1 and 2. Since this axis also rotates on swiveling, starting from the axis z, the axis z' or z" shown in FIG. 3 results after swiveling. Overall a large number of x-ray images is obtained in which the same direction does not have poor resolution throughout when reconstructing a 3D image record.

Basically all reconstruction methods can be used to produce a 3D image record, which represents the structure of the patient 16, wherein the taken set of x-ray images is used as the starting point. The reconstruction method does not necessarily have to differ from those used for the partial tomosyntheses. With filtered back projection a separate filter can be used for example for each sequence of x-ray images which corresponds to a respective swivel position in FIG. 3. However, it is also possible to define a comprehensive filter and to evaluate all x-ray image data jointly and at the same time. When using an iterative method for reconstructing the 3D image record x-ray images are naturally all included equally without a distinction being made as to within which sequence these x-ray images were taken.

Determining the filter using simulated or measured test objects can also take place using iterative reconstruction, as is illustrated in the above-mentioned application DE 10 2005 050917. The filters can also be designed in this case for individual scanning or equally and advantageously for overall scanning respectively.

The invention claimed is:

1. A method for generating a 3D image data of an object, comprising:

taking a first sequence of x-ray images of the object along a first straight line movement of an x-ray source and an x-ray detector relative to the object;

taking a further sequence of x-ray images of the object along a further straight line movement of the x-ray source and the x-ray detector relative to the object;

swiveling the x-ray source and the x-ray detector without taking any x-ray images between taking the first and the further sequences of the x-ray images;

moving the object along the straight lines while taking the first and the further sequences of the x-ray images; and generating the 3D image data based on the first and the further sequences of x-ray images by a reconstruction method for medically examining the object.

2. The method as claimed in claim 1, wherein the 3D image data comprises entries for a plurality of partial volumes and the entries are subsequently added to the first and the further sequences of x-ray images for each partial volume.

3. The method as claimed in claim 1, wherein a filtered rear projection method is used as the reconstruction method.

4. The method as claimed in claim 3, wherein a separate filter is used for the first and the further sequences of x-ray images.

5. The method as claimed in claim 3, wherein one filter is used for the first and the further sequences of x-ray images.

6. The method as claimed in claim 5, wherein:
a test 3D image data is generated for a test object with a known 3D structure before taking the first and the further sequences of x-ray images of the object,
the generated test 3D image data is compared with the known 3D structure of the test object, and
the one filter is determined based on the comparison.

7. The method as claimed in claim 6, wherein the test 3D image data is generated by steps of taking a first test sequence of x-ray images of the test object, swiveling the x-ray source and the x-ray detector, and taking a further test sequence of x-ray images of the test object.

8. The method as claimed in claim 1, wherein an iterative method is used as the reconstruction method.

9. A system for taking x-ray images of an object, comprising:
an x-ray source;
an x-ray detector that takes a first and a further sequences of x-ray images of the object along a straight line; and
a robot arm that:
fastens the x-ray source and the x-ray detector,
moves the x-ray source and the x-ray detector along the straight line while taking the first and the further sequences of x-ray images of the object,
swivels the x-ray source and the x-ray detector without taking any x-ray images between taking the first and the further sequences of x-ray images of the object; and
a table that supports the object and moves the object along the straight line while taking the first and the further sequence of x-ray images of the object.

10. The system as claimed in claim 9, wherein the x-ray source and the x-ray detector are swiveled about an axis and straightly moved along the axis.

11. A system for taking x-ray images of an object, comprising:
an x-ray source;
an x-ray detector that takes a first and a further sequences of x-ray images of the object along a straight line;
a C-arm that fastens the x-ray source and the x-ray detector and swivels the x-ray source and the x-ray detector without taking any x-ray images between taking the first and the further sequences of x-ray images of the object; and
a table that supports the object and moves the object along the straight line while taking the first and the further sequence of x-ray images of the object.

12. The system as claimed in claim 11, wherein the x-ray source and the x-ray detector are swiveled about an axis and the first and the further straight line movements take place along the axis.

13. The system as claimed in claim 11, wherein the first and the further sequences of x-ray images are taken in opposite directions.

14. The system as claimed in claim 11, wherein the x-ray source and the x-ray detector are arranged to a robot arm that swivels the x-ray source and the x-ray detector about an axis and moves the x-ray source and the x-ray detector along the axis.

15. The system as claimed in claim 14, wherein the x-ray source and the x-ray detector are moved in same or opposite directions.

16. The system as claimed in claim 11, wherein the x-ray source and the x-ray detector are arranged to an x-ray C-arm that swivels the x-ray source and the x-ray detector about an axis and the object is moved along the axis.

17. The system as claimed in claim 11, wherein the x-ray source is coupled with the x-ray detector.

18. The system as claimed in claim 11, further comprising a control unit that activates the x-ray source and x-ray detector and drives a motor for moving and swiveling the C-arm.

19. The system as claimed in claim 11, further comprising a computing unit that generates a 3D image data of the object based on the first and the further sequences of x-ray images by a reconstruction method.

20. The system as claimed in claim 11, wherein the x-ray source and the x-ray detector are swiveled about an axis and the object is straightly moved along the axis.

* * * * *